United States Patent [19]

Hoekstra

[11] Patent Number: 5,705,377
[45] Date of Patent: *Jan. 6, 1998

[54] TYROSINE KINASE

[75] Inventor: Merl F. Hoekstra, Leucadia, Calif.

[73] Assignee: The Salk Institute for Biological Studies, La Jolla, Calif.

[*] Notice: The portion of the term of this patent subsequent to May 6, 2014, has been disclaimed.

[21] Appl. No.: 447,408

[22] Filed: May 23, 1995

Related U.S. Application Data

[63] Continuation of Ser. No. 728,783, Jul. 3, 1991, abandoned.

[51] Int. Cl.$^6$ .................. C12N 1/00; C12N 5/00; C12N 9/00; C12N 9/12
[52] U.S. Cl. .................. 435/194; 435/320.1; 435/254.11; 435/183; 435/325; 435/410; 435/252.3; 536/23.2
[58] Field of Search .................. 536/23.2; 435/194, 435/320.1, 240.1, 254.11, 252.3, 188, 325, 410

[56] References Cited

PUBLICATIONS

Hoekstra et al. 1991. Science 253 1031–1034.
Toda et al (1987) Cell 50 277–287.
Lathe (1985) J. Mol. Biol. 183:1–12.
Donella-Deana et al (1985) Biochim Biophys Acta 829 180–187.
Singh et al (1985) Febs Letters 190: 84–88.
Szyszka et al 1985 Biochem. Biophys Acta 838,
Hoekstra, M.F., et al. J. Cell. Biochem. Suppl. 15A p. 156 (1991).
Berger, S.L. et al. Methods in Enzymology 152 pp. 393–506 (1987).
Haynes, et al.; DNA Repair and Mutagenesis in Yeast; Dept. of Biology, York University, Toronto, Canada, pp. 371–414.
Hanks, et al.; The Protein Kinase Family: Conserved Features . . . ; Science, vol. 241, Jul. 1988, pp. 42–52.

Malone, et al.; The RAD52 gene is required for homothallic interconversion . . . ; Proc.Natl.Acad.Sci. USA vol. 77, 503–507.

Courey, et al.; Analysis of Spl In Vivo Reveals Multiple Transcriptional Domains . . . ; Cell. vol. 55, 887–898, Dec. 2 1988.

Weiffenbach, et al.; Homothallic Mating Type Switching . . . ; Molecular and Cellular Biology, Jun. 1981, pp. 522–534, vol. 1, #6.

Roussou, et al.; Transcriptional–Translatioanl Regulatory Circuit . . . ; Molecular and CellularBiology, May 1988, 2131–2139.

Coffman, et al.; Xotch, the Xenopus Homolog of Drosophila Notch; Science, vol. 249, Sep. 1990, pp. 1438–1441.

Sagata, et al.; Function of c–mos proto–oncogene product . . . ; Nature, vol. 335, Oct. 6, 1988, pp. 519–525.

Russell, et al.; Negative Regulation of Mitosis by wee1$^+$. . . ; Cell, vol. 49, 559–567, May 22, 1987.

E. Hollingsworth, Jr., et al., DNA metabolism gene CDC7 from yeast . . . ; Proc. Natl. Acad. Sci. USA vol. 87, 6272–6276; Aug. 1990.

Coinfection of insect cells with recombinant baculovirus expressing pp60v–src results in the activation of a serine–specific protein kinase pp90rsk. Vik et al. Proc Natl Acad Sci U S A Apr. 1990, 87 (7) pp. 2685–2689.

(List continued on next page.)

*Primary Examiner*—Robert A. Wax
*Assistant Examiner*—Gabriele E. Bugaisky
*Attorney, Agent, or Firm*—Marshall, O'Toole, Gerstein, Murray & Borun

[57] ABSTRACT

Tyrosine kinase mutant and wild-type genes useful in screening compositions which may affect DNA double-strand break repair activity.

6 Claims, 2 Drawing Sheets

OTHER PUBLICATIONS

A newly synthesized selective casein kinase 1 inhibitor, N-(2-aminoethyl)-5-chloroquinoline-S-sulfonamide, and affinity purification of casein kinase 1 from bovine testis. Chijiwa et al., J. Biol. Chem. 25 Mar. 1989, 264 (9) pp. 4924–4927.

The application of the polymerase chain reaction to cloning members of the protein tyrosine kinase family. Wilks et al. Gene 1989 85 pp. 67–74.

Sambrook et al. Molecular Cloning: a Laboratory Manual, vol. 2, Cold Spring Harbor Press, pp. 9.47–9.58, 11.47–11.57 1989.

FIGURE 1A

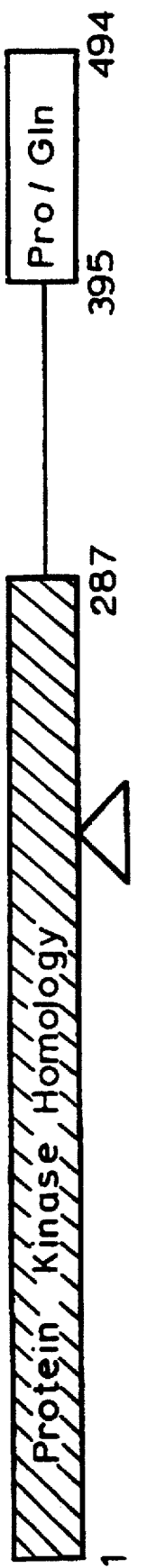

TYROSINE KINASE

This is a Continuation of U.S. application Ser. No. 07/728,783, filed Jul. 3, 1991, now abandoned.

BACKGROUND OF THE INVENTION

1. Field of The Invention

This invention relates generally to the molecular cloning of genes which can be used in toxicity assays and, specifically, to the isolation of a mammalian DNA recombination and repair gene which can be used in an assay to screen various compositions which affect DNA repair.

2. Related Art

Chromosomes experience single-stranded or double-stranded breaks as a result of energy-rich radiation, chemical agents, as well as spontaneous breaks occurring during replication among others. Although genes present in the chromosomes undergo continuous damage, repair, exchange, transposition, and splicing, certain enzymes protect or restore the specific base sequences of the chromosome.

The repair of DNA damage is a complex process that involves the coordination of a large number of gene products. This complexity is in part dependent upon both the form of DNA damage and cell cycle progression. For example, in response to ultraviolet (UV) irradiation, cells can employ photoreactivation or excision repair functions to correct genetic lesions. The repair of strand breaks, such as those created by X-rays, can proceed through recombinational mechanisms. For many forms of DNA damage, the cell is induced to arrest in the G2 phase of the cell cycle. During this G2 arrest, lesions are repaired to ensure chromosomal integrity prior to mitotic segregation.

Since the transfer of genetic information from generation to generation is dependent on the integrity of DNA, it is important to identify those gene products which affect or regulate genetic recombination and repair. Through the use of organisms with specific genetic mutations, the normal functional gene can be obtained, molecularly cloned, and the gene products studied.

Phenotypic complementation, as a way of identifying homologous normal functional genes, is widely used. For example, the human homologue of the yeast cell cycle control gene, cdc 2, was cloned by expressing a human cDNA library in *Schizosaccharomyces pombe* and selecting those clones which could complement a mutation in the yeast cdc 2 gene (Lee, et al., *Nature*, 327:31, 1987). A mammalian gene capable of reverting the heat shock sensitivity of the RAS2$^{val19}$ gene of yeast, has also been cloned by using complementation (Colicelli, et al, *Proc. Nat'l. Acad. Sci. USA*, 86.:3599, 1989). A rat brain cDNA library was used to clone a mammalian cDNA that can complement the loss of growth control associated with the activated RAS2 gene in yeast. The gene, DPD (dunce-like phosphodiesterase), encodes a high-affinity cAMP phosphodiesterase.

In eukaryotes such as *Saccharomyces cerevisiae*, genetic studies have defined repair-deficient mutants which have allowed the identification of more than 30 radiation-sensitive (RAD) mutants (Haynes, et al., in *Molecular Biology of the Yeast Saccharomyces*, pp. 371, 1981; J. Game in *Yeast Genetics: Fundamental and Applied Aspects*, pp. 109, 1983). These mutants can be grouped into three classes depending upon their sensitivities. These classes broadly define excision-repair, error-prone repair, and recombinational-repair functions. The molecular characterization of yeast RAD genes has increased the understanding of the enzymatic machinery involved in excision repair, as well as the arrest of cell division by DNA damage.

The understanding of RAD genes and their expression products has become increasingly important as research continues to develop more effective therapeutic compositions. Often these new compositions appear quite effective against a particular disease condition, such as certain tumors, but prove to be too toxic for in vivo therapy in an animal having the disease. Indeed, these compositions can actually increase the likelihood of mutagenesis.

Most agents that are mutagenic or carcinogenic are in themselves unreactive, but are broken down to reactive intermediates in vivo. It is these reactive intermediates which interact with DNA to produce a mutation. This event is thought to be the initial step in chemical carcinogenesis. Mutations in a large number of genes affect the cellular response to agents that damage DNA. In all likelihood, many of these mutated genes encode enzymes that participate in DNA repair systems. Consequently, when the repair system is compromised, the cells become extremely sensitive to toxic agents. Although the DNA may revert to normal when DNA repair mechanisms operate successfully, the failure of such mechanisms can result in a transformed tumor cell which continues to proliferate.

Although there are currently available tests to determine the toxicity or mutagenicity of chemical agents and compositions, there are limitations in both laboratory screening procedures and animal toxicity tests. These limitations include extrapolating laboratory data from animals to humans. There is often a large measure of uncertainty when attempting to correlate the results obtained in laboratory animals with effects in human subjects. In most cases, doses of the test drug have been used in the animal which are too high to be safely administered to humans. In addition, some types of toxicity can be detected if the drug is administered in a particular species, yet may be missed if the experiment is not done in the correct animal species. Moreover, many currently available laboratory tests are incapable of detecting certain types of toxic manifestations which occur in man.

Drugs are also routinely tested for their mutagenic potential using microorganisms in the screening assay. The popular test developed by Ames and colleagues (Ames, et al, *Mutat. Res.*:31,347, 1975) uses *Salmonella typhimurium* containing a mutant gene for histidine synthesis. This bacterial strain cannot grow in a histidine deficient medium unless a reverse mutation is induced by exposure to a particular agent. The Ames test is rapid and sensitive, however, its usefulness in predicting carcinogenic or mutagenic potential of chemical substances in human is unclear.

In summary, limitations and uncertainties of existing laboratory tests fail to provide an accurate method of examining the effects of a composition on DNA integrity. In view of this, a considerable need exists for screening methodologies which are inexpensive, rapid, and contain the relevant gene from the animal which is to be treated with the composition. Such methods provide a direct assay to determine if a composition interferes with the DNA repair system of a cell.

SUMMARY OF THE INVENTION

The present invention arose from the discovery of a novel protein which is involved in repair of DNA strand breaks. Although this protein has kinase activity, it is the only kinase known to promote repair of DNA strand breaks occurring at a specific nucleotide sequence and allow normal mitotic recombination. The identification of the normal, or "wild-type", protein kinase was made possible by the isolation of a yeast mutant (hrr25) defective in repairing DNA strand breaks, but still capable of promoting normal mitotic recombination. The wild-type gene (HRR25) was isolated by screening a DNA library for nucleotide sequences which could restore the ability to repair DNA breaks.

A major advantage of the present invention is that it now enables identification of functionally analogous wild-type proteins from other species, especially humans. The identification of such foreign protein provides the further advantage of allowing their use in a screening method designed to examine the effect of various compositions on the DNA break repair promoting activity of the foreign protein.

BRIEF DESCRIPTION OF THE DRAWINGS

FIG. 1(A) presents an alignment of the predicted amino acid sequence of HRR25 with the catalytic domains of yeast CDC28, yeast KSS1 and human RAF1 protein kinases.

FIG. 1(B) shows a schematic representation of the structure of HRR25 with the protein kinase region of homology in a shaded box and the proline (P) and glutamine (Q) rich C-terminus represented in an open box.

DETAILED DESCRIPTION OF THE PREFERRED EMBODIMENT

The present invention relates to a DNA recombination and repair gene which can be used in an assay system to examine the effects of various compositions on DNA integrity. The invention also provides a DNA sequence encoding a polypeptide which promotes normal mitotic recombination, but is defective in tyrosine kinase activity and essentially unable to repair DNA strand breaks. This defective DNA sequence is highly useful for identifying other DNA sequences which encode proteins with functional tyrosine kinase activity. These functional sequences, which can be characterized by their ability to restore DNA strand breaks, permit the screening of compositions to determine whether a particular composition has an effect on the restoration of such repair activity. In addition, the present invention relates to the polypeptide encoded by the defective DNA sequence, as well as the polypeptide encoded by the functional wild-type DNA.

In order to identify a DNA sequence encoding a polypeptide with tyrosine kinase activity, a method is provided whereby a DNA library is screened for nucleotide sequences capable of restoring DNA strand break repair in a mutant lacking such activity. A method is further provided for identifying a composition which affects the activity of a mammalian polypeptide having tyrosine kinase activity, wherein the polypeptide is capable of restoring DNA double-strand break repair activity in a mutant lacking such activity.

In general, the defective protein kinase can be characterized by its ability to promote normal mitotic recombination, while being essentially unable to repair DNA double-strand break including that which occurs at the cleavage site:

```
        ↓
    CAACAG
    GTTGTC
         ↑
```

The DNA double-strand breaks which the defective protein kinase is essentially unable to repair can be induced by various means, including endonucleases, x-rays, or radiomimetic agents including alkylating agents. Preferred endonucleases are those which recognize the same nucleotide cleavage site as endonuclease HO. Radiomimetic alkylating agents having methylmethane sulfonate activity are preferred. Those of skill in the art will be able to identify other agents which induce the appropriate DNA strand breaks without undue experimentation.

The present invention specifically discloses mutants sensitive to continuous expression of the DNA double-strand endonuclease HO, which codes for a 65 kDa site-specific endonuclease that initiates mating type interconversion (Kostriken, et al, *Cold Spring Harbor Symp. Quant. Biol.*, 49:89, 1984). These mutants are important to understanding the functions involved in recognizing and repairing damaged chromosomes. This invention also discloses a yeast wild-type DNA recombination and repair gene called HRR25 (HO and/or radiation repair). Homozygous mutant strains, hrr25-1, are sensitive to methylmethane sulfonate and X-rays, but not UV irradiation. The wild-type gene encodes a novel protein kinase, homologous to other serine/threonine kinases, which appears critical in activation of DNA repair functions by phosphorylation.

The HRR25 kinase is important for normal cell growth, nuclear segregation, DNA repair and meiosis, and deletion of HRR25 results in cell cycle defects. These phenotypes, coupled with the sequence similarities between the HRR25 kinase and the Raf/c-mos protein kinase subgroup suggest that HRR25 might play a similar role in *S. cerevisiae* growth and development. The defects in DNA strand break repair and the aberrant growth properties revealed by mutations in HRR25 kinase, expands the role that protein kinases may play and places HRR25 in a functional category of proteins associated with DNA metabolism.

The development of specific DNA sequences encoding protein kinase polypeptides of the invention can be accomplished using a variety of techniques. For example, methods which can be employed include (1) isolation of a double-stranded DNA sequence from the genomic DNA of the eukaryote; (2) chemical synthesis of a DNA sequence to provide the necessary codons for the polypeptide of interest; and (3) in vitro synthesis of a double stranded DNA sequence by reverse transcription of mRNA isolated from a eukaryotic donor cell. In the latter case, a double stranded DNA complement of mRNA is eventually formed which is generally referred to as cDNA.

Figure 1A:
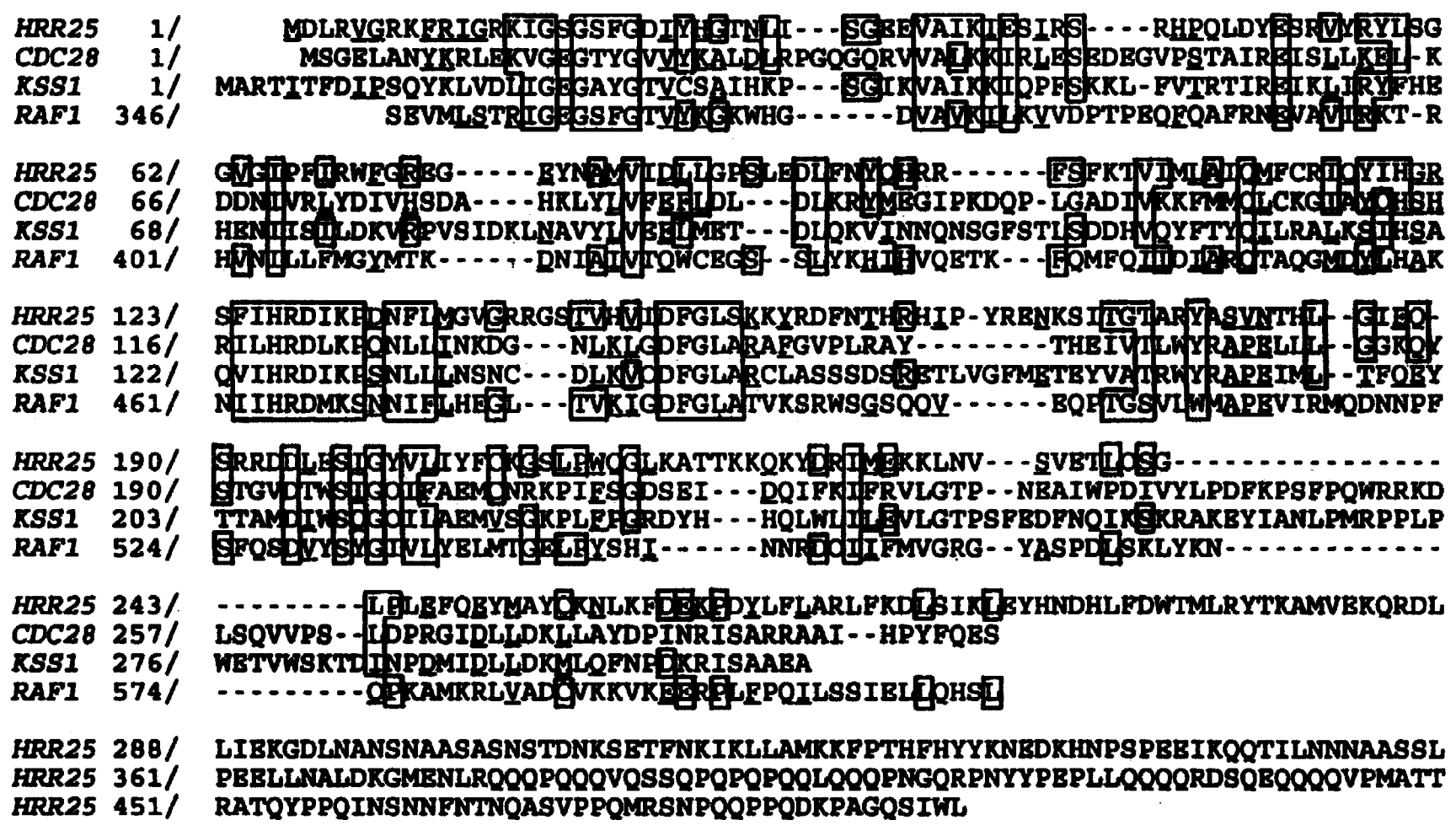

The novel DNA sequences of the invention include all sequences useful in providing for expression in prokaryotic or eukaryotic host cells of polypeptides which exhibit the functional characteristics of the novel protein kinase of the invention. These DNA sequences comprise: (a) the DNA sequences as set forth in FIG. 1 or their complementary strands; (b) DNA sequences which encode an amino acid sequence with at least about 35% homology in the protein kinase domain with the amino acid sequences encoded by the DNA sequences defined in (a) or fragments thereof; and (c) DNA sequences defined in (a) and (b) above. Specifically embraced in (b) are genomic DNA sequences which encode allelic variant forms. Part (c) specifically embraces the manufacture of DNA sequences which encode fragments of the protein kinase and analogs of the protein kinase wherein the DNA sequences thereof may incorporate codons which facilitate translation of mRNA. Also included in part (c) are DNA sequences which are degenerate as a result of the genetic code.

Since the DNA sequence of the invention encodes essentially the entire protein kinase molecule, it is now a routine matter to prepare, subclone, and express smaller polypeptide fragments of DNA from this or a corresponding DNA sequence. The term "polypeptide" denotes any sequence of amino acids having the characteristic activity of the mutant or wild-type protein kinase of the invention, wherein the sequence of amino acids is encoded by all or part of the DNA sequences of the invention.

The polypeptide resulting from expression of the DNA sequence of the invention can be further characterized as being free from association with other eukaryotic polypeptides or other contaminants which might otherwise be associated with the protein kinase in its natural cellular environment.

Isolation and purification of microbially expressed polypeptides provided by the invention may be by conventional means including, preparative chromatographic separations and immunological separations involving monoclonal and/or polyclonal antibody preparation.

In general, expression vectors useful in the present invention contain a promotor sequence which facilitates the efficient transcription of the inserted eukaryotic genetic sequence. The expression vector typically contains an origin of replication, a promoter, and a terminator, as well as specific genes which are capable of providing phenotypic selection of the transformed cells. The transformed hosts can be grown in fermentors and cultured according to techniques known in the art to achieve optimal cell growth. The polypeptides of the invention can then be isolated from the growth medium, cellular lysates, or cellular membrane fractions.

The DNA sequences of the present invention can be expressed in vivo in either prokaryotes or eukaryotes. Methods of expressing DNA sequences containing eukaryotic coding sequences in prokaryotes are well known in the art. Biologically functional viral and plasmid DNA vectors used to incorporate DNA sequences of the invention, for expression and replication in the host cell are well known in the art. For example, DNA can be inserted in yeast using appropriate vectors and introducing the product into the host cells. Various shuttle vectors for the expression of foreign genes in yeast have been reported (Heinemann, et al, *Nature*, 340:205, 1989; Rose, et al., *Gene*, 60:237, 1987). Those of skill in the art will know of appropriate techniques for obtaining gene expression in both prokaryotes and eukaryotes, or can readily ascertain such techniques, without undue experimentation.

Hosts include microbial, yeast and mammalian host organisms. Thus, the term "host" is meant to include not only prokaryotes, but also such eukaryotes such as yeast, filamentous fungi, as well as plant and animal cells which can replicate and express an intron-free DNA sequence of the invention. The term also includes any progeny of the subject cell. It is understood that not all progeny are identical to the parental cell since there may be mutations that occur at replication. However, such progeny are included when the terms above are used.

Transformation with recombinant DNA may be carried out by conventional techniques well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl could be used in the reaction. Transformation can also be performed after forming a protoplast of the host cell.

Where the host is a eukaryote, various methods of DNA transfer can be used. These include transfection of DNA by calcium phosphate-precipitates, conventional mechanical procedures such as microinjection, insertion of a plasmid encased in liposomes, spheroplast electroporation, salt mediated transformation of unicellular organisms or the use of virus vectors.

Analysis of eukaryotic DNA has been greatly simplified since eukaryotic DNA can be cloned in prokaryotes using vectors well known in the art. Such cloned sequences can be obtained easily in large amounts and can be altered in vivo by bacterial genetic techniques and in vitro by specific enzyme modifications. To determine the effects of these experimentally induced changes on the function and expression of eukaryotic genes, the rearranged sequences must be taken out of the bacteria in which they were cloned and reintroduced into a eukaryotic organism. Since there are still many functions in eukaryotic cells which are absent in prokaryotes, (e.g., localization of ATP-generating systems to mitochondria, association of DNA with histones, mitosis and meiosis, and differentiation of cells), the genetic control of such functions must be assessed in a eukaryotic environment. Cloning genes from other eukaryotes in yeast has been useful for analyzing the cloned eukaryotic genes as well as other yeast genes. A number of different yeast vectors have been constructed for this purpose. All vectors replicate in *E. coli*, which is important for amplification of the vector DNA. All vectors contain markers, e.g., LEU 2, HIS 3, URA 3, that can be selected easily in yeast. In addition, these vectors also carry antibiotic resistance markers for use in *E. coli*.

Many strategies for cloning human homologues of known yeast genes are known in the art. These include, but are not limited to: 1) low stringency hybridization to detect shared nucleotide sequences; 2) antibody screening of expression libraries to detect shared structural features; and 3) complementation of mutants to detect genes with similar functions.

For purposes of the present invention, protein kinases which are homologous can be identified by structural as well as functional similarity. Structural similarity can be determined, for example, by assessing amino acid homology or by screening with antibody, especially a monoclonal antibody, which recognizes a unique epitope present on the protein kinases of the invention. When amino acid homology is used as criteria to establish structural similarity, those amino acid sequences which have homology of at least about 35% in the protein kinase domain are considered to be essentially the same as the amino acid sequences of the invention. When homologous amino acid sequences are evaluated based on functional characteristics, then a homologous amino acid sequence is considered equivalent to the amino acid sequence of the invention when the homologous sequence is essentially unable to repair (in the case of the repair defective mutant gene) or able to repair (in the case of the natural gene), DNA double-strand breaks, including that which occurs at a nucleotide cleavage site $$\downarrow$$
CAACAG
GTTGTC
$$\uparrow$$

and when the homologous amino acid sequence allows normal mitotic recombination.

This invention preferably uses the functional screening method whereby genes are cloned from plasmid libraries by complementation of a recessive marker. A recipient strain such as *Saccharomyces cerevisiae* is constructed that carries a recessive mutation in the gene of interest. This strain is then transformed with a plasmid, for example, pYES2

(Invitrogen, San Diego, Calif.) containing the wild-type genomic DNA or cDNA. The clone carrying the gene of interest can then be selected by replica plating to a medium that distinguishes mutant from wild-type phenotypes for the gene of interest. The plasmid can then be extracted from the clone and the DNA studied. Several yeast vectors allow the application of complementation systems to go beyond isolation of yeast genes. Genes from a wide variety of species can be isolated using these vectors. In such systems, DNA sequences from any source are cloned into a vector and can be screened directly in yeast for activities that will complement specific yeast mutations.

In a preferred embodiment, the present invention uses a mutation in yeast, the hrr25 mutation, which was identified by sensitivity to DNA double-strand breaks induced by the HO endonuclease. The genomic DNA which complements this mutation was isolated by transforming the hrr25 strain with a DNA library and subsequently screening for methylmethane sulfonate (MMS) resistance. Alternately, functional genes from a variety of mammalian species can now be cloned using the system described.

Yeast genes can be cloned by a variety of techniques, including use of purified RNA as hybridization probes, differential hybridization of regulated RNA transcripts, antibody screening, transposon mutagenesis, cross suppression of mutant phenotypes, cross hybridization with heterologous cDNA or oligonucleotide probes, as well as by complementation in E. coli Minor modifications of the primary amino acid sequence may result in proteins which have substantially equivalent or enhanced activity as compared to the sequence set forth in FIG. 1(A) and Sequence I.D. No. 2. The modifications may be deliberate, as by site-directed mutagenesis, or may be spontaneous by HRR25 producing organisms. All of these modifications are included in the invention as long as HRR25 activity is retained. Substitution of an aspartic acid residue for a glycine acid residue at position 151 in the sequence shown in FIG. 1 identifies the mutant hrr25.

Antibodies provided by the present invention are immunoreactive with the mutant polypeptides and/or the naturally occurring protein kinase. Antibody which consist essentially of numerous monoclonal antibodies with different epitopic specificities, as well as distinct monoclonal antibody preparations are provided. Monoclonal antibody is made from antigen containing fragments of the polypeptide by methods well known in the art (Kohler, G. et al, Nature 256:495, 1975; Current Protocols in Molecular Biology, Ausubel, F. et al., ed.,1989).

The invention also discloses a method for identifying a composition which affects the activity of a polypeptide having tyrosine kinase activity. The polypeptide is capable of restoring DNA double-strand break repair activity in host cells containing the hrr25 gene. The composition and the polypeptide are incubated in combination with host cells for a period of time and under conditions sufficient to allow the components to interact, then subsequently monitoring the change in tyrosine kinase activity, for example, by decreased repair of DNA double-strand breaks. The DNA strand breaks are induced, for example, by a radiomimetic agent, such as methylmethane sulfonate, x-rays, or by endonuclease like HO. Other means of inducing double-strand breaks that are well known in the art may be employed as well.

The following examples are intended to illustrate but not limit the invention. While they are typical of those that might be used, other procedures known to those skilled in the art may alternatively be used.

EXAMPLE 1

Isolation of hrr25

S. cerevisiae strain K264-5B (MAT α ho ura3 can1$^R$ tyr1 his7 lys2 ade5 met13 trp5 leu1 ade5) was employed for the mutant isolation. The yeast were transformed according to standard procedures with a URA3-based integrating plasmid that contained a GAL1,10-regulated HO endonuclease and a transformant was mutagenized to approximately 50% survival with ethyl methanesulfonate (EMS), as described (Current Protocols in Molecular Biology, supra). The culture was spread onto glycerol-containing rich medium (YPG, to avoid petites), colonies were allowed to form at 30° C., and plates were replicated to glucose (HO repressing) and galactose (HO inducing) media. Mutants were identified by their inability to grow on galactose. Approximately 200 mutants were chosen for initial characterization and 62 maintained the gal- phenotype through repeated single colony purification. Among these, many were not complemented by various gal mutants. The remainder (25 mutants) were surveyed for overlapping DNA repair defects by determining sensitivity to ultraviolet (UV) irradiation and to methyl methane sulfonate (MMS). This screening method identified five alleles of known rad mutations and one new mutation. This new mutation hrr25-1 (HO and/or radiation repair), presented severe defects and was studied further.

A recessive DNA repair defect is conferred by hrr25-1 that includes sensitivity to MMS. Hrr25-1 strains also show sensitivity at 5–20 Krad X-irradiation similar to that observed with mutations in the radiation repair genes RAD50 and RAD52 (Cole, et al, Mol. Cell. Biol., 9:3101, 1989). The hrr25-1 strains are no more sensitive to UV irradiation than wild type and are not temperature sensitive for growth at 37° C. Unlike hypo- and hyper-rec rad mutants which have several of the hrr25-1 phenotypes, hrr25-1 strains undergo normal mitotic recombination (Cole, et al., Mol. Cell. Biol., 9:3101, 1989). Spontaneous gene conversion and crossing-over were the same for homozygous hrr25-1 and wild type strains. However, HRR25 is required for the correct completion of meiosis. The hrr25-1 homozygotes showed less than 1% spores (tetranucleate cells) under conditions that produced 75–80% spores in an isogenic wild type strain. The hrr25-1 mutation could be complemented by a number of radiation sensitive mutations (rad6, 50, 52, 54, and 57) that present some of the hrr25 phenotypes, suggesting that hrr25-1 is a newly uncovered rad-like mutation and not one of these previously described genes. These results also indicate that HRR25 plays a role in DNA repair and meiosis, but is not specifically required for the repair of spontaneous mitotic lesions by recombination.

EXAMPLE 2

Isolation of HRR25

The HRR25 gene was obtained by complementing for MMS sensitivity using a yeast genomic library constructed in the plasmid YCp50 (Rose, et al., Gene, 60:237, 1987). An hrr25-1 strain, MHML 3-36d (ura3 hrr25), was transformed by standard methods (Nickoloff, et al., J. Mol. Biol., 207:527, 1989) to uracil prototrophy, transformants were amplified on media without uracil and replicated to media containing 0.01% MMS. Among 1200 transformants, a single MMS resistant isolate was identified. Complementation for MMS sensitivity was found to segregate with the plasmid as determined by methods known in the art.

A 12 kb genomic fragment was identified and complementing activity was localized to a 3.1 kb BamHI-Sa/1 fragment by transposon mutagenesis and subcloning. This region complemented DNA repair defects as well as meiotic deficiencies. Gene targeting experiments linked this cloned region to hrr25-1. Transposon insertion mutations within the BamHI-Sa/1 fragment replaced into the cognate HRR25 genomic locus did not complement hrr25-1 for MMS sensitivity, whereas adjacent chromosomal insertions outside the complementing region segregated in repulsion when crossed against hrr25-1.

Mini-Tn10LUK transposons (Huisman, et al., *Genetics*, 116:191, 1987) were used to delineate the approximate location of HRR25 on the 12 kb BamHI-Sa/1 fragment. Insertions located to the left hand 9 kb (of the 12 kb genomic fragment) did not inactivate complementation of hrr25-1 MMS resistance compared with the un-mutagenized plasmid. Two insertions, located near an EcoRV site in the right hand 2 kb inactivated complementation. HRR25 complementation activity was localized to a 3.4 kb Sa/1 fragment. Approximately 300 bp of this fragment (right hand side of the 12 kb) were part of the pBR322 tetracycline resistance gene (between the BamHI site of pBR322-based YCp50). The HRR25 open reading frame spans an internal region across an EcoRV site and two Bg/11 sites within the right terminal 3 kb.

The DNA sequence of the 3.1 kb fragment revealed a centrally located open reading frame of 1482 nucleotide. A transposon insertion mutation in this open reading frame inactivated HRR25 complementation whereas insertions elsewhere in the 12 kb clone did not affect HRR25 complementation. Transposon-mediated disruption of HRR25 also revealed several phenotypes not seen with hrr25-1. As expected, a Tn10-based LUK transposon insertion (Huisman, et al., *Genetics*, 116:191, 1987) into the middle of plasmid-borne HRR25 coding region inactivated complementation for MMS sensitivity. Transplacement of this insertion into the genomic HRR25 gene revealed a severe growth defect in addition to MMS sensitivity and meiotic inviability. This severe growth defect was not observed with hrr25-1 strains. Wild type HRR25 strains doubled in rich media at 30° C. every 80–90 minutes whereas isogenic hrr25::LUK strains and hrr25Δ doubled every 9–12 hours. hrr25-1 had a doubling time of 2–4 hours.

To determine whether the mutant phenotypes revealed by the hrr::LUK disruption allele represent a null phenotype, the entire HRR25 coding sequence was deleted. Briefly, deletion of the HRR25 coding sequence employed a hisG::URA3::hisG cassette (Alani, et al., *Genetics*, 116:541, 1988). The 3.1 kb HRR25 Sa/1 fragment was cloned into pBluescript (Stratagene, La Jolla, Calif.). This plasmid was digested with Bg/11 and the two Bg/11 fragments that span the entire HRR25 gene and its flanking sequences were deleted. Into this deletion was introduced the 3.8 kb BamHI-Bg/11 hisG::URA3::hisG fragment from pNKY51 to create the hrr25Δ allele. Sa/1 digestion yielded a linearized fragment that deleted the entire HRR25 locus. Yeast carrying the deletion-disruption allele (hrr25Δ) showed phenotypes identical to those with the hrr25::LUK allele for all properties examined, including MMS sensitivity, slow growth, and the sporulation defect, indicating that wild-type HRR25 protein is associated with these processes and that the hrr25::LUK allele does not indirectly interfere with DNA repair, growth or sporulation. In direct parallel comparisons, the hrr25::LUK and hrr25Δ alleles behaved identically.

Yeast strain MFH14 (MATa/MATα, ura3/ura3) was transformed with Bg/11-linearized YCp50-HRR25::LUK to uracil prototrophy, heterozygous disruption of HRR25 was verified by Southern blot analysis, the diploid was sporulated by starvation for nitrogen and fermentable carbon source, tetrads dissected and cells allowed to germinate at 30° C. for 7 days. After a normal germination period of 2 days, the severe growth defect of hrr25::LUK suggested that the deletion of HRR25 was lethal. However, microscopic examination of segregants revealed that hrr25::LUK germinating cells grew slowly and in every case examined (20/20 tetrads), slow growth, MMS sensitivity, and uracil prototrophy co-segregated. A color variation was seen with diploid MFH14 segregants, due to mutations in adenine biosynthesis. MFH14 is ade5/ADE5 ade2/ade2. An ade5/ade2 strain was white, while an ADE5/ade2 strain was red.

EXAMPLE 3

Sequence and Structure of the HRR25 Gene

DNA sequencing of both strands of the HRR25 gene was done by unidirectional deletions employing Sequenase (USB, Cleveland, Ohio) and Exo-Meth (Stratagene, La Jolla, Calif.) procedures as described by the manufacturers. FIG. 1A, shows the location of the prolines and glutamines at the C-terminus as indicated by asterisks, and the limits of homology to protein kinase catalytic domains. FIG. 1B shows a schematic representation of the structure of HRR25. The protein kinase homology is represented by a shaded region while the P/Q rich region is indicated by crosshatchings. The mutant, hrr25, can be distinguished from HRR25 by one amino acid substitution. At position 151, an aspartic acid is substituted for glycine.

The predicted translation product of HRR25 revealed an unexpected feature for a rad-like DNA repair function. HRR25 contains the hallmark signatures of sequence homology with the catalytic domain of serine/threonine protein kinase superfamily members (Hanks, et al., *Science*, 241:42, 1988). For comparison, the HRR25 translation product was aligned with the catalytic domains for two subgroups of yeast protein kinases, the CDC28/cdc2 group and the KSS1/FUS3 group. Located between amino acids 15 and 30 is a region that contains the conserved GXGXXG region. Just C-terminal to this region is a conserved lysine and glutamic acid present in most known kinases. These regions are thought to function in the nucleotide binding and phosphotransfer steps of the kinase reaction (Hanks, et al., *Science*, 241:42,1988). Between amino acid residues 120 to 150 are regions containing the HRD and DFG motifs, also found in most protein kinase family members. In addition, sequence examination of all known serine/threonine kinases indicates that HRR25 shares some additional similarities with the Raf/PKS/mos subgroup (Hanks, et al., *Science*, 241:42, 1988). The strongest homologies can be found in areas around the GXGXXG, DFG, and DXXSXG conserved regions in protein kinase catalytic domains.

The functional relevance of the observed sequence similarity between HRR25 and protein kinases was studied by altering specific residues within the HRR25 kinase domain and examining the phenotypic consequences of these changes. A lysine at position 38 ($Lys^{38}$) was mutated to an arginine residue by site directed mutagenesis, by methods known in the art. The mutagenic oligonucleotide was:

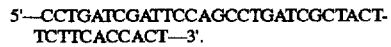
5'—CCTGATCGATTCCAGCCTGATCGCTACT-TCTTCACCACT—3'.

$Lys^{38}$ in HRR25 corresponds to the lysine found in all known protein kinases, and this subdomain is involved in ATP binding. Mutations at the conserved lysine in protein kinases such as v-src, v-mos, and DBF2 inactivate these proteins. The mutant hrr25-$Lys^{38}$ allele was incapable of complementing hrr25-1, hrr25::LUK, and hrr25Δ alleles for all properties examined, an indication that the HRR25 kinase domain is required for in vivo function of HRR25.

The predicted HRR25 translation product has a number of notable features outside the region of homology to protein kinase catalytic domains. For example, the last 100 amino acids is proline and glutamine rich, containing 50 of these residues. Other proteins with regions rich in these two amino acids include the transcription factors Sp1, jun, and HAP2, steroid hormone receptors, the *S. pombe* ran1 kinase, and mak-male germ cell-associated kinase (Courey, et al., *Cell*, 55:887, 1988; Bohmann, et al., *Science*, 238:1386, 1987; Roussou, et al., *Mol. Cell. Biol.*, 8:2132, 1988; Arriza, et al., *Science*, 237:268, 1987; Matsushime, et al., *Mol. Cell. Biol.*, 10:2261, 1990). In the case of Sp1 and jun, the proline-glutamine regions are involved in transactivation, whereas the P/Q region in the human mineralocorticoid receptor is thought to serve as an intramolecular bridge. This proline-glutamine region in HRR25 might function as a structural feature for substrate interaction, or for subcellular localization. Also, the glutamine richness of this region is similar to the opa or M-repeat seen in the Drosophila and Xenopus Notch/Xotch proteins (Wharton, et al., *Cell*, 40:55, 1985; Coffman, et al., *Science*, 249:1438, 1990). The function of the opa repeat is not certain, but it is found in several Drosophila genes. Lastly, the sequence TKKQKY at the C-terminal end of the region homologous to protein kinases is similar to the nuclear localizing signal of SV40 large T antigen and yeast histone H2B (Silver, et al., *J. Cell. Biol.*, 109:983, 1989; Moreland, et al., *Mol. Cell. Biol.*, 7:4048, 1987).

EXAMPLE 4

Microscopic Analysis of Germinating and Proliferating hrr25 Cells

Photomicrographs of HRR25 and hrr25::LUK colonies were taken after germination on rich medium. An MFH14 hrr25::LUK heterozygous transformant was dissected onto a thin film of YPD rich medium on a sterilized microscope slide and segregants were allowed to germinate under a coverslip by incubating the slide in a moist 30° C. chamber. Photographs of colonies were taken after 2 days of growth. Phase contrast and DAPI staining of proliferating HRR25Δ and hrr25::LUK cells were compared. Cells were inoculated into YPD rich medium and grown at 30° C. to a mid-log density of $1-3\times10^7$ cells/ml, briefly sonicated to disrupt clumps, fixed with formaldehyde, and stained with DAPI (Williamson, et al., *Meth. Cell. Biol.*, 12:335, 1975). Many cells with hrr25::LUK lacked DAPI stainable nuclei.

Microscopic examination of germinating and actively growing mid-log phase hrr25::LUK cells revealed aberrant cellular morphologies. Transposon disruption of HRR25 resulted in large cells, and 25–40% of cells were filamentous or extended. DAPI nuclear staining (Williamson, et al., *Meth. Cell. Biol.*, 12:335, 1975) of mid-log populations showed that orderly cell cycle progression in hrr25 mutants was lost. There were a large number of cells lacking DAPI-stainable nuclei which, by single cell manipulations proved to be inviable. Consistent with this nuclear segregation defect, the plating efficiency of hrr25::LUK haploids was also reduced to 75–80% of wild type. However, this reduction in plating efficiency is insufficient to account for the severe growth rate reduction. Plating efficiency was measured from mid-log phase cells by comparing the efficiency of colony formation on rich medium relative to the total number of cells determined by hemocytometer count. Cell populations were analyzed for DNA content distribution by flow cytometric analysis following staining with propidium iodide as described (Hutter, et al. *J. Gen. Microbiol.*, 113:369, 1979). Cell sorting analysis showed that a large number of the cells in a haploid hrr25::LUK population were delayed in the cell cycle and exhibited G2 DNA content, but the population was not arrested uniformly in the cell cycle.

EXAMPLE 5

Sequence Comparison of HRR25 with CDC28, KSS1, AND RAF1

The predicted translation product of HRR25 was compared with the catalytic domains of several members of the serine/threonine protein kinase superfamily and the results are set out in FIG. 1(A). Initial sequence comparisons employed the UWGCG programs (Devereux, at al., *Nuc. Acids. Res.*, 12:387, 1984), whereas subgroup comparisons used the methods of Hanks, et al., supra. HRR25 contains all eleven subdomains described by Hanks, et al., supra. Structurally similar groupings were compared in the sequence comparisons. These included nonpolar chain R groups, aromatic or ring-containing R groups, small R groups with near neutral polarity, acidic R groups, uncharged polar R groups, and basic polar R groups.

CDC28 and KSS1 represent members of two subgroups of serine/threonine protein kinases in yeast. CDC28 is involved in cell cycle regulation while KSS1 acts in the regulation of the yeast mating pathway. HRR25 shows 21% identity and 41% similarity to CDC28 and 19% identity and 43% similarity to KSS1. HRR25 shows highest similarity to members of the Raf1/PKS/Mos family of protein kinases. Through the catalytic domain, HRR25 shows 30% identity and 49% similarity to Raf1.

SUMMARY OF SEQUENCES

Sequence I.D. No. 1 is the nucleic acid sequence (and the deduced amino acid sequence) of a genomic fragment encoding a yeast-derived tyrosine kinase of the present invention.

Sequence I.D. No. 2 is the deduced amino acid sequence of a yeast-derived tyrosine kinase of the present invention.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3098 base pairs

-continued ( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Tyrosine Kinase ( i x ) FEATURE:
( A ) NAME/KEY: CDS
( B ) LOCATION: 879..2364

( x i ) SEQUENCE DESCRIPTION: SEQ ID NO:1:

| | |
|---|---|
| GTCGACTCGC CAATCACCAA GTTCTTATCC CACATCCGAC CAGTGTCTGA GTCATGGTTT | 60 |
| ACCACCACCA TACCATCGCT GGTCATTTGT AAATCCGTTT CTATTACATC AGCACCTGCT | 120 |
| GCATAAGCCT TCTCAAATGC TAGTAGCGTA TTTTCAGGAT ATCTTGCTTT AAAAGCTCTG | 180 |
| TGGCCCACAA TTTCAACCAT CCTCGTGTCC TTGTTGTTAT CTTACACTTC TTATTTATCA | 240 |
| ATAACACTAG TAACATCAAC AACACCAATT TTATATCTCC CTTAATTGTA TACTAAAAGA | 300 |
| TCTAAACCAA TTCGGTATTG TCCTCGATAC GGCATGCGTA TAAAGAGATA TAATTAAAAG | 360 |
| AGGTTATAGT CACGTGATGC AGATTACCCG CAACAGTACC ACAAAATGGA TACCATCTAA | 420 |
| TTGCTATAAA AGGCTCCTAT ATACGAATAA CTACCACTGG ATCGACGATT ATTTCGTGGC | 480 |
| AATCATATAC CACTGTGAAG AGTTACTGCA ACTCTCGCTT TGTTTCAACG CTTCTTCCCG | 540 |
| TCTGTGTATT TACTACTAAT AGGCAGCCCA CGTTTGAATT TCTTTTTTTC TGGAGAATTT | 600 |
| TTGGTGCAAC GAGGAAAAGG AGACGAAGAA AAAAAGTTGA ACACGACCA CATATATGGA | 660 |
| ACGTGGTTGA AATACAAAGA GAAGAAAGGT TCGACACTCG AGGAAAGCAT TTGGTGGTGA | 720 |
| AAACACATCT TAGTAGCATC TTTAAACCTC TGTTGGGTAC TTAGAAAAAT ATTTCCAGAC | 780 |
| TTCAAGGATA AAAAAAGTCG AAAAGTTACG ACATATTCGA CCAAAAAAAA AAACCAAAAA | 840 |
| GAAAAGATAT ATTTATAGAA AGGATACATT AAAAAGAG ATG GAC TTA AGA GTA | 893 |
| Met Asp Leu Arg Val | |
| 1 5 | |

| | |
|---|---|
| GGA AGG AAA TTT CGT ATT GGC AGG AAG ATT GGG AGT GGT TCC TTT GGT | 941 |
| Gly Arg Lys Phe Arg Ile Gly Arg Lys Ile Gly Ser Gly Ser Phe Gly | |
| 10 15 20 | |
| GAC ATT TAC CAC GGC ACG AAC TTA ATT AGT GGT GAA GAA GTA GCC ATC | 989 |
| Asp Ile Tyr His Gly Thr Asn Leu Ile Ser Gly Glu Glu Val Ala Ile | |
| 25 30 35 | |
| AAG CTG GAA TCG ATC AGG TCC AGA CAT CCT CAA TTG GAC TAT GAG TCC | 1037 |
| Lys Leu Glu Ser Ile Arg Ser Arg His Pro Gln Leu Asp Tyr Glu Ser | |
| 40 45 50 | |
| CGC GTC TAC AGA TAC TTA AGC GGT GGT GTG GGA ATC CCG TTC ATC AGA | 1085 |
| Arg Val Tyr Arg Tyr Leu Ser Gly Gly Val Gly Ile Pro Phe Ile Arg | |
| 55 60 65 | |
| TGG TTT GGC AGA GAG GGT GAA TAT AAT GCT ATG GTC ATC GAT CTT CTA | 1133 |
| Trp Phe Gly Arg Glu Gly Glu Tyr Asn Ala Met Val Ile Asp Leu Leu | |
| 70 75 80 85 | |
| GGC CCA TCT TTG GAA GAT TTA TTC AAC TAC TGT CAC AGA AGG TTC TCC | 1181 |
| Gly Pro Ser Leu Glu Asp Leu Phe Asn Tyr Cys His Arg Arg Phe Ser | |
| 90 95 100 | |
| TTT AAG ACG GTT ATC ATG CTG GCT TTG CAA ATG TTT TGC CGT ATT CAG | 1229 |
| Phe Lys Thr Val Ile Met Leu Ala Leu Gln Met Phe Cys Arg Ile Gln | |
| 105 110 115 | |
| TAT ATA CAT GGA AGG TCG TTC ATT CAT AGA GAT ATC AAA CCA GAC AAC | 1277 |
| Tyr Ile His Gly Arg Ser Phe Ile His Arg Asp Ile Lys Pro Asp Asn | |
| 120 125 130 | |
| TTT TTA ATG GGG GTA GGA CGC CGT GGT AGC ACC GTT CAT GTT ATT GAT | 1325 |

```
            Phe Leu Met Gly Val Gly Arg Arg Gly Ser Thr Val His Val Ile Asp
                135             140                 145

TTC GGT CTA TCA AAG AAA TAC CGA GAT TTC AAC ACA CAT CGT CAT ATT           1373
Phe Gly Leu Ser Lys Lys Tyr Arg Asp Phe Asn Thr His Arg His Ile
150             155                 160                 165

CCT TAC AGG GAG AAC AAG TCC TTG ACA GGT ACA GCT CGT TAT GCA AGT           1421
Pro Tyr Arg Glu Asn Lys Ser Leu Thr Gly Thr Ala Arg Tyr Ala Ser
                170                 175                 180

GTC AAT ACG CAT CTT GGA ATA GAG CAA AGT AGA AGA GAT GAC TTA GAA           1469
Val Asn Thr His Leu Gly Ile Glu Gln Ser Arg Arg Asp Asp Leu Glu
            185                 190                 195

TCA CTA GGT TAT GTC TTG ATC TAT TTT TGT AAG GGT TCT TTG CCA TGG           1517
Ser Leu Gly Tyr Val Leu Ile Tyr Phe Cys Lys Gly Ser Leu Pro Trp
        200                 205                 210

CAG GGT TTG AAA GCA ACC ACC AAG AAA CAA AAG TAT GAT CGT ATC ATG           1565
Gln Gly Leu Lys Ala Thr Thr Lys Lys Gln Lys Tyr Asp Arg Ile Met
    215                 220                 225

GAA AAG AAA TTA AAC GTT AGC GTG GAA ACT CTA TGT TCA GGT TTA CCA           1613
Glu Lys Lys Leu Asn Val Ser Val Glu Thr Leu Cys Ser Gly Leu Pro
230                 235                 240                 245

TTA GAG TTT CAA GAA TAT ATG GCT TAC TGT AAG AAT TTG AAA TTC GAT           1661
Leu Glu Phe Gln Glu Tyr Met Ala Tyr Cys Lys Asn Leu Lys Phe Asp
                250                 255                 260

GAG AAG CCA GAT TAT TTG TTC TTG GCA AGG CTG TTT AAA GAT CTG AGT           1709
Glu Lys Pro Asp Tyr Leu Phe Leu Ala Arg Leu Phe Lys Asp Leu Ser
            265                 270                 275

ATT AAA CTA GAG TAT CAC AAC GAC CAC TTG TTC GAT TGG ACA ATG TTG           1757
Ile Lys Leu Glu Tyr His Asn Asp His Leu Phe Asp Trp Thr Met Leu
        280                 285                 290

CGT TAC ACA AAG GCG ATG GTG GAG AAG CAA AGG GAC CTC CTC ATC GAA           1805
Arg Tyr Thr Lys Ala Met Val Glu Lys Gln Arg Asp Leu Leu Ile Glu
    295                 300                 305

AAA GGT GAT TTG AAC GCA AAT AGC AAT GCA GCA AGT GCA AGT AAC AGC           1853
Lys Gly Asp Leu Asn Ala Asn Ser Asn Ala Ala Ser Ala Ser Asn Ser
310                 315                 320                 325

ACA GAC AAC AAG TCT GAA ACT TTC AAC AAG ATT AAA CTG TTA GCC ATG           1901
Thr Asp Asn Lys Ser Glu Thr Phe Asn Lys Ile Lys Leu Leu Ala Met
                330                 335                 340

AAG AAA TTC CCC ACC CAT TTC CAC TAT TAC AAG AAT GAA GAC AAA CAT           1949
Lys Lys Phe Pro Thr His Phe His Tyr Tyr Lys Asn Glu Asp Lys His
            345                 350                 355

AAT CCT TCA CCA GAA GAG ATC AAA CAA CAA ACT ATC TTG AAT AAT AAT           1997
Asn Pro Ser Pro Glu Glu Ile Lys Gln Gln Thr Ile Leu Asn Asn Asn
        360                 365                 370

GCA GCC TCT TCT TTA CCA GAG GAA TTA TTG AAC GCA CTA GAT AAA GGT           2045
Ala Ala Ser Ser Leu Pro Glu Glu Leu Leu Asn Ala Leu Asp Lys Gly
    375                 380                 385

ATG GAA AAC TTG AGA CAA CAG CAG CCG CAG CAG CAG GTC CAA AGT TCG           2093
Met Glu Asn Leu Arg Gln Gln Gln Pro Gln Gln Gln Val Gln Ser Ser
390                 395                 400                 405

CAG CCA CAA CCA CAG CCC CAA CAG CTA CAG CAG CAA CCA AAT GGC CAA           2141
Gln Pro Gln Pro Gln Pro Gln Gln Leu Gln Gln Gln Pro Asn Gly Gln
                410                 415                 420

AGA CCA AAT TAT TAT CCT GAA CCG TTA CTA CAG CAG CAA CAA AGA GAT           2189
Arg Pro Asn Tyr Tyr Pro Glu Pro Leu Leu Gln Gln Gln Gln Arg Asp
            425                 430                 435

TCT CAG GAG CAA CAG CAG CAA GTT CCG ATG GCT ACA ACC AGG GCT ACT           2237
Ser Gln Glu Gln Gln Gln Gln Val Pro Met Ala Thr Thr Arg Ala Thr
        440                 445                 450

CAG TAT CCC CCA CAA ATA AAC AGC AAT AAT TTT AAT ACT AAT CAA GCA           2285
```

-continued

```
        Gln Tyr Pro Pro Gln Ile Asn Ser Asn Asn Phe Asn Thr Asn Gln Ala
            455                 460                 465

TCT GTA CCT CCA CAA ATG AGA TCT AAT CCA CAA CAG CCG CCT CAA GAT         2333
Ser Val Pro Pro Gln Met Arg Ser Asn Pro Gln Gln Pro Pro Gln Asp
470                 475                 480                 485

AAA CCA GCT GGC CAG TCA ATT TGG TTG TAA G CAACATATAT TGCTCAAAAC         2384
Lys Pro Ala Gly Gln Ser Ile Trp Leu
            490                 495

GCACAAAAAT AAACATATGT ATATATAGAC ATACACACAC ACATATATAT ATATATATTA       2444

TTATTATTAT TTACATATAC GTACACACAA TTCCATATCG AGTTAATATA TACAATTCTG       2504

GCCTTCTTAC CTAAAAAGAT GATAGCTAAA AGAACCACTT TTTTTATGCA TTTTTTTCTT       2564

CGGGAAGGAA ATTAAGGGGG AGCGGAGCAC CTCTTGGCCA ATTTGTTTTT TTTTTATGTA       2624

ATAAAGGGCT AACGATCGAA GATCAATCAC GAATATTGGA CGGTTTTAAA GGAGGGCCTC       2684

TGAGAAGACA GCATCAATTC GTATTTTCGA TAATTAACTT GCCTTATAGT GTCTGATTAG       2744

GAAACAATCA CGAGACGATA ACGACGGAAT ACCAAGGAAG TTTGTGCAAA TATACAGCCG       2804

GCACAAACAG CAGCTTCACT CAGGTTAACT CACATACTGT TGAAAATTGT CGGTATGGAA       2864

TTCGTTGCAG AAAGGGCTCA GCCAGTTGGT CAAACAATCC AGCAGCAAAA TGTTAATACT       2924

TACGGGCAAG GCGTCCTACA ACCGCATCAT GATTTACAGC AGCGACAACA ACAACAACAG       2984

CAGCGTCAGC ATCAACAACT GCTGACGTCT CAGTTGCCCC AGAAATCTCT CGTATCCAAA       3044

GGCAAATATA CACTACATGA CTTCCAGATT ATGAGAACGC TTGGTACTGG ATCC            3098
```

( 2 ) INFORMATION FOR SEQ ID NO:2:

( i ) SEQUENCE CHARACTERISTICS:
    ( A ) LENGTH: 494 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Asp Leu Arg Val Gly Arg Lys Phe Arg Ile Gly Arg Lys Ile Gly
1               5                   10                  15

Ser Gly Ser Phe Gly Asp Ile Tyr His Gly Thr Asn Leu Ile Ser Gly
            20                  25                  30

Glu Glu Val Ala Ile Lys Leu Glu Ser Ile Arg Ser Arg His Pro Gln
        35                  40                  45

Leu Asp Tyr Glu Ser Arg Val Tyr Arg Tyr Leu Ser Gly Gly Val Gly
    50                  55                  60

Ile Pro Phe Ile Arg Trp Phe Gly Arg Glu Gly Glu Tyr Asn Ala Met
65                  70                  75                  80

Val Ile Asp Leu Leu Gly Pro Ser Leu Glu Asp Leu Phe Asn Tyr Cys
                85                  90                  95

His Arg Arg Phe Ser Phe Lys Thr Val Ile Met Leu Ala Leu Gln Met
            100                 105                 110

Phe Cys Arg Ile Gln Tyr Ile His Gly Arg Ser Phe Ile His Arg Asp
        115                 120                 125

Ile Lys Pro Asp Asn Phe Leu Met Gly Val Gly Arg Arg Gly Ser Thr
    130                 135                 140

Val His Val Ile Asp Phe Gly Leu Ser Lys Lys Tyr Arg Asp Phe Asn
145                 150                 155                 160

Thr His Arg His Ile Pro Tyr Arg Glu Asn Lys Ser Leu Thr Gly Thr
                165                 170                 175
```

```
Ala Arg Tyr Ala  Ser Val Asn Thr His  Leu Gly Ile Glu Gln  Ser Arg
            180                  185                 190

Arg Asp Asp  Leu Glu Ser Leu Gly  Tyr Val Leu Ile Tyr  Phe Cys Lys
        195              200              205

Gly Ser Leu Pro Trp Gln Gly  Leu Lys Ala Thr Thr  Lys Lys Gln Lys
        210              215              220

Tyr Asp Arg Ile Met Glu  Lys Lys Leu Asn Val  Ser Val Glu Thr  Leu
225                 230              235                      240

Cys Ser Gly Leu Pro  Leu Glu Phe Gln Glu  Tyr Met Ala Tyr  Cys Lys
                245                 250                 255

Asn Leu Lys Phe  Asp Glu Lys Pro Asp  Tyr Leu Phe Leu Ala  Arg Leu
            260                 265                 270

Phe Lys Asp Leu Ser Ile Lys Leu  Glu Tyr His Asn Asp  His Leu Phe
        275                 280                 285

Asp Trp Thr Met Leu Arg Tyr  Thr Lys Ala Met Val  Glu Lys Gln Arg
        290             295              300

Asp Leu Leu Ile Glu Lys  Gly Asp Leu Asn Ala  Asn Ser Asn Ala  Ala
305                 310              315                      320

Ser Ala Ser Asn Ser  Thr Asp Asn Lys Ser  Glu Thr Phe Asn  Lys Ile
                325                 330                 335

Lys Leu Leu Ala Met  Lys Lys Phe Pro  Thr His Phe His Tyr  Tyr Lys
            340                 345                350

Asn Glu Asp Lys His Asn Pro  Ser Pro Glu Glu Ile  Lys Gln Gln Thr
        355              360              365

Ile Leu Asn Asn Asn Ala Ala  Ser Ser Leu Pro Glu  Leu Leu Asn
        370             375              380

Ala Leu Asp Lys Gly Met  Glu Asn Leu Arg Gln  Gln Gln Pro Gln  Gln
385              390              395                       400

Gln Val Gln Ser Ser  Gln Pro Gln Pro Gln  Pro Gln Gln Leu  Gln Gln
                405                 410                 415

Gln Pro Asn Gly  Gln Arg Pro Asn Tyr  Tyr Pro Glu Pro Leu  Leu Gln
            420                 425                 430

Gln Gln Gln Arg Asp Ser Gln Glu  Gln Gln Gln Gln Val  Pro Met Ala
        435             440              445

Thr Thr Arg Ala Thr Gln Tyr  Pro Pro Gln Ile Asn  Ser Asn Asn Phe
    450             455              460

Asn Thr Asn Gln Ala Ser Val  Pro Pro Gln Met Arg  Ser Asn Pro Gln
465             470              475                      480

Gln Pro Pro Gln Asp  Lys Pro Ala Gly Gln  Ser Ile Trp Leu
            485              490                     495
```

The invention now being fully described, it will be apparent to one of ordinary skill in the art that various changes and modifications can be made without departing from the spirit or scope of the invention.

What is claimed is:

1. An isolated polynucleotide encoding the *S. cerevisiae* HRR25 protein kinase polypeptide of Sequence I.D. No. 2.

2. An isolated polynucleotide encoding the polypeptide of Sequence I.D. No. 2 wherein an aspartic acid residue replaces the glycine residue at position 151.

3. An isolated polynucleotide encoding only a polypeptide having greater than 35 percent amino acid sequence homology to the protein kinase domain amino acid residues 1–287 of SEQ ID NO: 2, wherein said polypeptide:

a) possesses protein kinase activity;
b) promotes normal mitotic recombination; and
c) promotes repair of a DNA strand break occurring at an HO endonuclease site.

4. A biologically functional plasmid or viral DNA vector comprising a DNA polypeptide according to claim 1, 2 or 3.

5. A host cell transformed or transfected with a DNA polynucleotide according to claim 1, 2, or 3.

6. A process for recombinant production of a protein kinase polypeptide comprising growing host cells according to claim 5 under nutrient conditions suitable to allow expression of the protein kinase therein.

* * * * *